United States Patent

Roewer et al.

Patent Number: 5,718,685
Date of Patent: Feb. 17, 1998

[54] STOMACH PROBE

[75] Inventors: Norbert Roewer, Hamburg; Volker Klute, Melsungen, both of Germany

[73] Assignee: B. Braun Melsungen AG, Melsungen, Germany

[21] Appl. No.: 825,655

[22] Filed: Apr. 3, 1997

Related U.S. Application Data

[63] Continuation of Ser. No. 515,494, Aug. 15, 1995, abandoned.

[30] Foreign Application Priority Data

Aug. 17, 1994 [DE] Germany ............ 9413272 U

[51] Int. Cl.$^6$ ............................. A61M 29/00
[52] U.S. Cl. ................. 604/100; 604/101; 604/175
[58] Field of Search ............. 604/96–101, 174–175; 606/192, 196

[56] References Cited

U.S. PATENT DOCUMENTS

| | | | |
|---|---|---|---|
| 2,667,875 | 2/1954 | Wallace | 128/349 |
| 4,335,723 | 6/1982 | Patel. | |
| 4,370,982 | 2/1983 | Reilly. | |
| 4,743,230 | 5/1988 | Nordquest | 604/97 |
| 4,758,221 | 7/1988 | Jureidini. | |
| 4,813,935 | 3/1989 | Haber et al.. | |
| 5,207,651 | 5/1993 | Snyder. | |
| 5,462,528 | 10/1995 | Roewer. | |

FOREIGN PATENT DOCUMENTS

| | | | |
|---|---|---|---|
| 0 217 559 A1 | 4/1987 | European Pat. Off. | A61M 25/00 |
| 24 12 533 A1 | 9/1975 | Germany | A61M 25/00 |

*Primary Examiner*—Mark Bockelman
*Attorney, Agent, or Firm*—Alix, Yale & Ristas, LLP

[57] ABSTRACT

A stomach probe has an aspiration tube (1) and a stomach balloon (7) which is to be held, by tensioning of the aspiration tube (1), in contact against the stomach wall (12) surrounding the cardiac orifice (5). The stomach balloon is connected to a pressure control device which is equipped to indicate at least two pressure stages, of which the lower one corresponds to the freely inflated state of the stomach balloon when the tube is untensioned, and the higher one corresponds to the tensioned state of the aspiration tube. The stomach balloon (7) is arranged on the aspiration tube at points which are at a short distance from each other, so that it assumes approximately a torus configuration in the inflated state. It is elastically resilient in the longitudinal direction of the tube.

8 Claims, 2 Drawing Sheets

STOMACH PROBE

This application is a continuation of application Ser. No. 08/515,494 filed on Aug. 15, 1995 now abandoned.

BACKGROUND AND SUMMARY OF THE INVENTION

A stomach probe is known my application, now U.S. Pat. No. 5,462,528, issued Oct. 31, 1995, and entitled "Stomach Tube", which has a stomach balloon which is to be held, by means of the tensioning of the aspiration tube, in sealing contact against the stomach wall surrounding the cardiac orifice. The sealing state is maintained by virtue of the fact that the tensioning of the aspiration tube is maintained by means of a nasal stopper. The stomach balloon is connected to a pressure control device which makes it possible in the following manner to check that the stomach balloon is in the correct position and that the tensioning of the aspiration tube is sufficient. After the probe has been introduced, the stomach balloon situated in the stomach is first inflated freely to a first, low, pressure stage, while the aspiration tube is slack. The aspiration tube is then tensioned, as a result of which the stomach balloon bears with corresponding pressure against the stomach wall. Its internal pressure in this case rises as the tensioning of the tube increases corresponding to the pressure with which the balloon bears on the stomach wall. When the pressure measurement device indicates that a second, higher, pressure stage has been reached, which is known to correspond to a contact pressure sufficient for the sealing, the state which has been reached is fixed by means of the nasal stopper.

In order to seal the contents of the stomach off sufficiently from the oesophagus, a certain minimum contact pressure is necessary. The tensile force on the tube is equal to the product of this pressure and the contact surface on which this pressure acts. In order to protect the patient, an attempt is made to keep this force as small as possible. It is also desirable for the arrangement consisting of aspiration tube and stomach balloon to have a high elasticity, so that a change in the length over which the aspiration tube is tensioned between the stomach and the nasal stopper, such as can occur, for example, when the position of the patient's body or head changes or a shift of the nasal stopper goes unobserved, has no effect or only a slight effect on the contact pressure prevailing between the stomach balloon and the wall of the stomach. However, with the known arrangement, the tensile force on the tube could not be effectively lowered, since, on the one hand, the contact pressure for an effective sealing may not fall below a certain minimum value, and, on the other hand, the balloon must be so large that it cannot escape unintentionally from the cardiac orifice. The result of this is that the minimum value of the tensile force prevailing in the tube is a considerable one.

The invention achieves a decrease in this force and an increase in the elasticity by virtue of the fact that the distance between the attachment points at which the two walls of the stomach balloon are secured on the aspiration tube is kept essentially smaller than the radial dimension of the tube, measured from its outermost circumference to the surface of the tube, the stomach balloon being designed such that it is elastically resilient in the longitudinal direction of the tube. The stated dimension ratios are to be measured when the balloon is inflated at the use pressure. The distance between the attachment points of the balloon walls is expediently no greater than two thirds of the stated radial dimension of the balloon. It is preferably in the order of magnitude of approximately half this value. The balloon according to the invention is also characterized in that the distance between the attachment points is smaller than the maximum expansion of the balloon in a direction parallel to the tube section passing through it, this distance being preferably no greater than two thirds of this expansion. The attachment points are understood as being those points at which the membrane forming the balloon stretches, under the internal pressure of the balloon, outwards and free of the tube.

The effect of the measure according to the invention is that the balloon does not have the outward appearance of a sphere or an ellipsoid, but instead approximately that of a torus. This has consequences on the one hand for the nature of the bearing of the balloon on the stomach wall, and on the other hand for the elasticity of the arrangement. First, the stomach balloon does not lie with full pressure over the whole surface on the stomach wall facing it and surrounding the cardiac orifice, but basically engages the stomach wall with an annular surface which is at a certain radial distance from the tube centre and the centre of the cardiac orifice. The radial width of this annular surface is also small. Inside the area enclosed by the annular surface and nearer the centre, the balloon does not touch the stomach wall or else touches it only with a lower pressure than on the annular surface. This is not a problem, since it suffices if the sealing contact pressure is obtained in the comparatively limited annular surface. The tensioning of the tube, with the same sealing effect, is therefore less than when using a spherical balloon.

Secondly, it has been found that the toroidal balloon has considerable elasticity in the longitudinal direction of the tube. The contact pressure end the internal pressure of the balloon change only slightly when the balloon deforms under the tensioning of the aspiration tube. This has the advantage that the sealing effect does not depend to such a great extent as in the known stomach probe on the position of the patient's head and body remaining stationary.

A further advantage of the invention lies in the fact that the balloon is less exposed to the risk of being pulled out through the cardiac orifice. It can therefore be equipped with a smaller diameter. As a result of this, the contact surface area is further reduced and the tensioning of the tube decreased.

U.S. Pat. No. 2,267,875 discloses a catheter with a toroidal retention balloon which, in contrast to the invention, is intended to be non-elastic. The particular advantages which are obtained when a toroidal balloon with elastic properties is used in the particular context of a stomach balloon, which seals upon tensioning of the tube, cannot be discerned from reading the stated specification.

This specification also teaches that the balloon is constructed from two film pieces which are essentially plane in the relaxed state and which are connected sealingly to one another at the outer edge and to the tube at the inner edge. This arrangement has the advantage, in the context of the invention, that the annular area of the balloon which is used for the sealing remains essentially free from folds.

The reduction, which is achieved according to the invention, in the tensioning prevailing in the aspiration tube is so considerable that in many cases a nasal stopper can be dispensed with in favour of an oesophagus balloon. This proposal is known per se from DE-A 24 12 553; but it has not been adopted in practice. In the known case, a spherical stomach balloon is used which can be sealed against the stomach wall only with comparatively great tensioning of the tube. However, an oesophagus balloon is unable to withstand such great tensioning of the tube, since on account of the sensitivity of the oesophagus it can bear on the latter only with slight force, and for this reason only a slight frictional force can be produced. Thus, since the tensioning of the tube is only slight, the stomach balloon cannot achieve a sufficient sealing effect. This was obviously also clear to the originator of the known probe since he proposes using the oesophagus balloon for additional sealing. But this too does not stand up to realistic testing since as a result of the sensitivity of the oesophagus the pressure which can be exerted there by the oesophagus balloon is so low that it does not permit an adequate sealing effect.

It is also known (U.S. Pat. No. 3,046,988) to use the combination of a stomach balloon and oesophagus balloon in order to staunch haemorrhages from superficial blood vessels at the cardiac orifice and in the oesophagus. Since the oesophagus balloon cannot hold the stomach balloon firmly in the intended position, a nasal stopper is provided.

The holding action of the oesophagus balloon need not be based solely on the friction with respect to the wall of the oesophagus. Instead, according to the invention, it is possible to provide for the oesophagus balloon to rest additionally or principally on the isthmus formed by the lower oesophageal sphincter. The distance between the stomach balloon and the oesophagus balloon is then dimensioned such that the oesophagus balloon assumes the position necessary for the supporting when the aspiration tube has the tensioning necessary for the correct position of the stomach balloon. In this respect it is of advantage that the stomach balloon according to the invention has a greater axial resiliency than conventional spherical or ellipsoid balloons, so that it can compensate for different anatomical sizes.

BRIEF DESCRIPTION OF THE DRAWINGS

The invention is explained in greater detail hereinbelow with reference to the drawing which represents an advantageous illustrative embodiment and in which.

DESCRIPTION OF A PREFERRED EMBODIMENT

Figure 1:
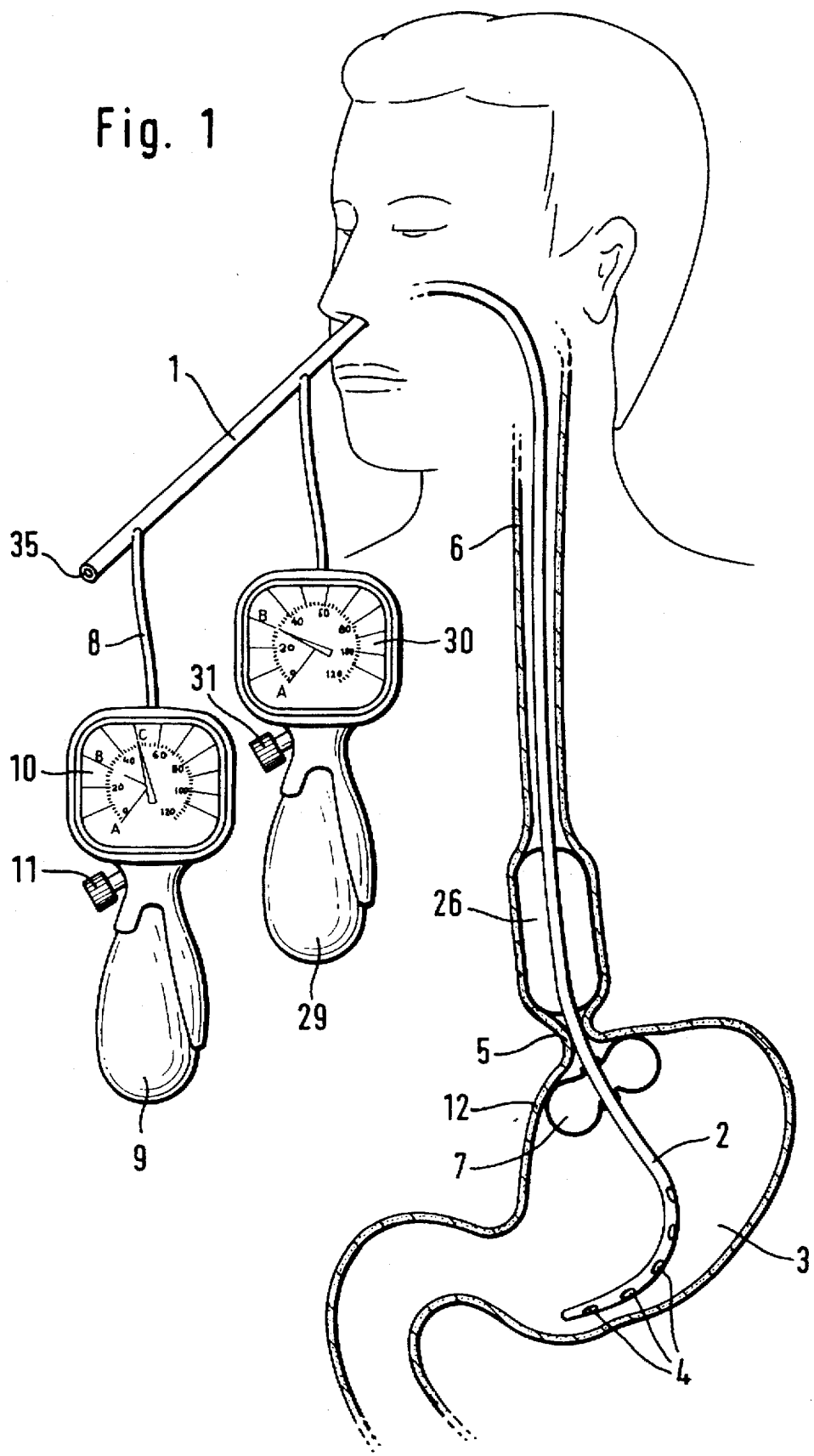
FIG. 1 shows an overall view.

The stomach probe comprises an aspiration tube 1 which has aspiration openings 4 in its end section 2 which is intended to lie free in the stomach 3, and which can be connected in a known manner to a suction apparatus via its free attachment end 35 in order to aspirate the contents of the stomach. In order to seal off the cardiac orifice 5, at which the lower sphincter of the oesophagus 6 forms an isthmus, a stomach balloon 7 is used whose inside is connected, via a special lumen provided on the aspiration tube, to the attachment tube 8, to which a hand pump 9 with manometer 10 and pressure relief screw 11 is attached. Together with the section 2 of the aspiration tube 1, the stomach balloon 7 is introduced in the uninflated state into the stomach, and is then inflated by means of the hand pump 9 with check valve from zero pressure (pressure stage A) to a low pressure of, for example, 20–30 mbar (pressure stage B). The airways which could lead to an escape of air from the balloon are then closed. In particular, the vent screw 11 is closed in this respect and subsequently remains closed. By pulling on the aspiration tube 1, the latter is tensioned, whereupon the stomach balloon 7 bears against the stomach wall 12 surrounding the cardiac orifice 5 and exerts a contact pressure which at its maximum is as great as the internal pressure in the stomach balloon 7. This internal pressure is greater, the more strongly the stomach balloon 7 bears against the stomach wall under the tensioning of the aspiration tube 1. It is checked by means of the manometer 10 and at pressure stage C should lie approximately 10–20 mbar higher than pressure stage B. The aspiration tube 1 is fixed in its position as soon as this pressure has been reached. Thus far, the device and its use are known in the prior art on which the invention is based.

The stomach balloon 7 has a shape which approximates that of a torus. This shape comes about because the points 13, 14 at which the walls 15, 16 of the stomach balloon 7 are secured on the aspiration tube 1 are at a small distance 17 from one another. This distance amounts, for example, to 12 mm in the case of a stomach balloon with an external diameter of 6 cm. It is at any rate smaller than the radial dimension 18 and that dimension 19 of the balloon measured parallel to the aspiration tube. It can be still smaller than in the example and can shrink to zero for example. The attachment points are to be regarded as those points at which the membrane forming the balloon lifts away from the aspiration tube 1 to form the balloon wall.

Figure 2:
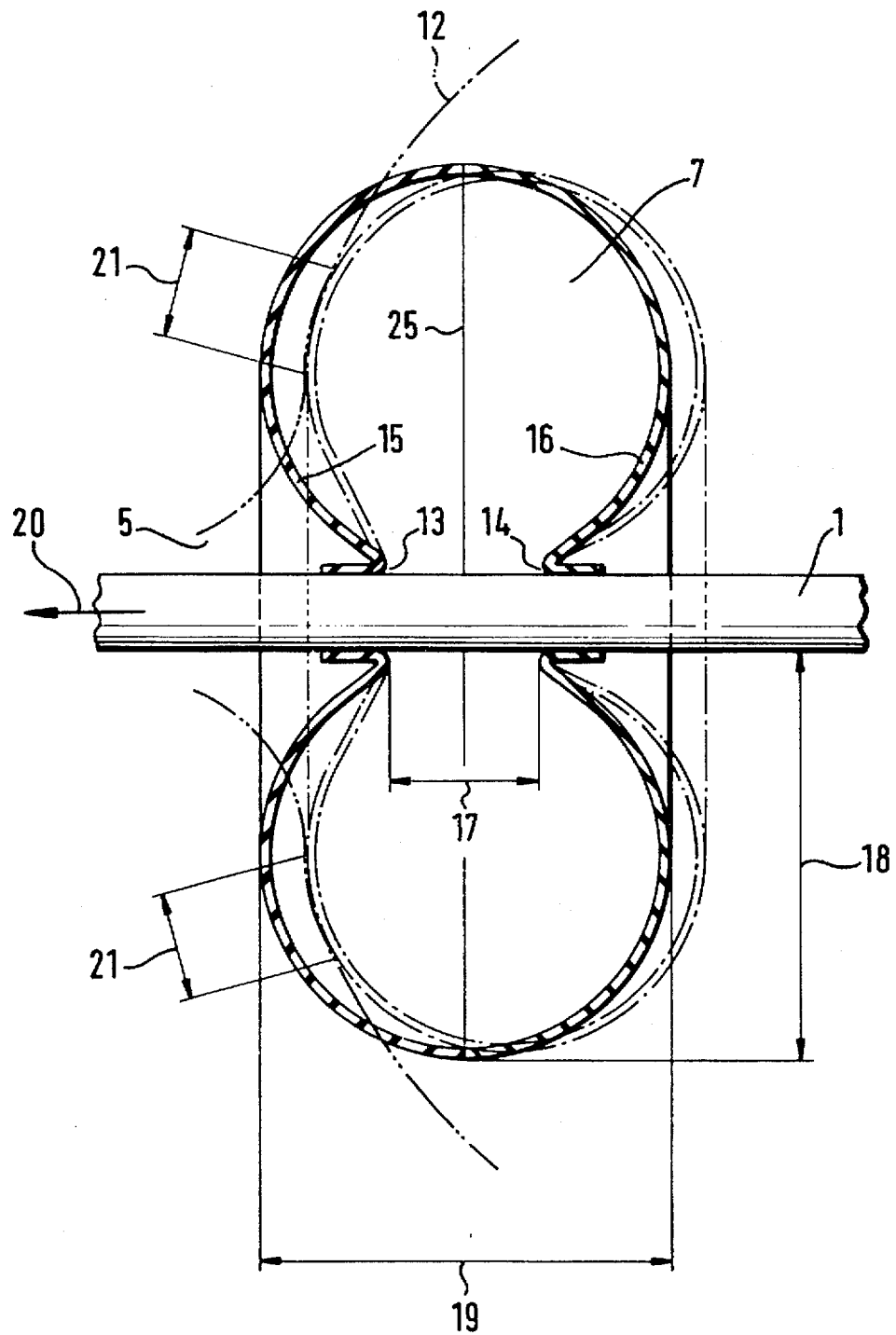
FIG. 2 shows a diagrammatic longitudinal section through the stomach balloon.

In the unpensioned, inflated state, the stomach balloon presents the longitudinal section configuration shown by full lines in FIG. 2. When the contact force of the stomach wall 12 acts on it as the aspiration tube 1 is tensioned by being pulled in the direction indicated by the arrow 20, it deforms in the way indicated by broken lines in FIG. 2, in which respect it exhibits a remarkable elasticity in the longitudinal direction of the tube. An annular surface 21, which is denoted in FIG. 2 by its radial dimension, in this case principally comes to bear on the stomach wall 12. The greatest pressure obtained in this contact surface is equal to the internal pressure of the stomach balloon. In the area which lies beside and radially within this annular surface, no contact takes place, or, if it does take place, the prevailing contact pressure is negligibly small. The size of the surface within which the internal pressure of the balloon acts as contact pressure on the stomach wall is accordingly very small. The tensile force 20 necessary in the aspiration tube 1 is also correspondingly small. Nevertheless, a sufficient sealing effect is obtained because the annular surface 21 reliably encloses the cardiac orifice, and the contact pressure necessary for a good sealing effect is obtained all around, and even with greater reliability than in the case of contact covering a large surface area.

Unlike the case of a spherical balloon, this contact surface extends virtually perpendicular to the direction of the aspiration tube 1 and for this reason exerts practically no widening wedge effect on the cardiac orifice. The stomach balloon according to the invention can therefore be designed for two reasons with a substantially smaller diameter than conventional spherical stomach balloons, on the one hand because the tensioning in the aspiration tube is less, and on the other hand because the opening wedge effect exerted by the balloon on the cardiac orifice is smaller. The result of this in turn is a reduction of the contact surface, which has a favourable effect on the extent of the required tensioning of the aspiration tube.

The stomach balloon 7 is made from two plane, round membrane blanks which are welded together at their outer circumference which, in the case of the inflated balloon according to FIG. 2, appears as the equatorial line 25.

The low tensioning of the aspiration tube achieved according to the invention is in any case agreeable for the patient, even if the aspiration tube is fixed with a nasal stopper. Moreover, the low tensioning of the aspiration tube makes it possible in many cases to effect fixing with an oesophagus balloon 26. The low friction already prevailing between the oesophagus balloon 26 and the oesophageal wall is often sufficient for this. Alternatively, or in addition to this, the oesophagus balloon is expediently arranged so that its lower end is supported on the isthmus of the oesophagus as formed at the cardiac orifice 5 by the lower sphincter of the oesophagus. The distance between the balloons 7 and 26 is dimensioned, taking into consideration average anatomical measurements, such that this support is effectively obtained. Individual differences in size can be compensated by the high elasticity of the stomach balloon. The surface of the oesophagus balloon 26 can be structured to promote friction, for example with a plurality of raised parts and depressions. In addition, it is expediently cylindrical in the inflated state, its diameter being chosen such that the desired contact tensioning and friction are obtained by the dilation of the oesophagus. To inflate the oesophagus balloon and to check its condition, a further hand pump 29 with manometer 30, check valve and vent screw 31 can be provided.

We claim:

1. A method of preventing reflux of stomach contents into the esophagus comprising the steps of
   a) providing a stomach probe comprising an aspiration tube suited for emptying the contents of the stomach, a stomach balloon permanently secured to the tube for sealing the stomach's cardiac orifice, and a pressure control device operatively connected to the balloon and equipped to indicate at least lower and higher pressure stages, the lower pressure stage corresponding to a freely inflated state of the stomach balloon when the tube is untensioned and the higher pressure stage corresponding to the tensioned state of the aspiration tube, the stomach balloon having two walls fixedly connected to the aspiration tube and spaced at their attachment points to the tube by a distance that is smaller than the radial balloon dimension between its outer circumference and the tube surface in the inflated state during the higher pressure stage and is smaller than the greatest expansion of the stomach balloon in a direction parallel to the section of the aspiration tube passing through it;
   b) introducing the stomach probe for a sufficient distance so that the balloon is positioned within the stomach;
   c) inflating the balloon to said lower pressure stage while the tube is untensioned whereby the balloon exhibits a toroidal shape;
   d) drawing the inflated balloon into engagement with the stomach wall to provide a narrow ring-like annular surface contact between the balloon and the stomach wall; and
   e) tensioning the tube to cause the balloon to effectively seal the stomach's cardiac orifice at a lower tube tension level than is required when using a spherically shaped balloon for sealing the cardiac orifice.

2. The method of claim 1 wherein the distance between the attachment points is no greater than two thirds of said radial dimension of said inflated stomach balloon.

3. The method of claim 1 wherein the balloon configuration provides elastic resilience in the longitudinal direction of the tube and the distance between the attachment points is no greater than two thirds of the greatest expansion of the stomach balloon in a direction parallel to the section of the aspiration tube passing through the balloon.

4. The method of claim 1 wherein the pressure at the higher pressure stage is at least about 10 mbar greater than the pressure at the lower pressure stage.

5. The method of claim 1 including the step of fixing the position of the aspiration tube after the tensioning thereof.

6. The method of claim 1 wherein the stomach probe includes an esophageal balloon secured to the tube at a spaced distance from the stomach balloon and the method includes the step of inflating the esophageal balloon to hold the aspiration tube in a tensioned condition.

7. The method of claim 6 wherein the distance between the stomach balloon and the esophageal balloon is such that the inflated esophageal balloon bears on the upper side of the lower esophageal sphincter.

8. The method of claim 6 wherein the esophageal balloon when inflated is generally cylindrical.

* * * * *